United States Patent [19]

Teasdale

[11] Patent Number: 5,243,721
[45] Date of Patent: Sep. 14, 1993

[54] INFLATABLE MATTRESS AND AIR SUPPLY WITH CHANGEOVER VALVE

[75] Inventor: Barry C. Teasdale, Stockport, England

[73] Assignees: Karomed Limited, Lancashire; S. Teasdale (Hospital) Equipment Limited, Cheshire, both of England

[21] Appl. No.: 930,198

[22] Filed: Aug. 14, 1992

[30] Foreign Application Priority Data

Aug. 16, 1991 [GB] United Kingdom ............ 9117825

[51] Int. Cl.[5] .......................................... A61G 7/04
[52] U.S. Cl. ........................................ 5/453; 5/455
[58] Field of Search .................. 5/453, 455, 449, 469

[56] References Cited

U.S. PATENT DOCUMENTS

| | | | |
|---|---|---|---|
| 2,998,817 | 9/1961 | Armstrong | 5/453 X |
| 4,193,149 | 3/1980 | Welch | 5/453 X |
| 4,653,130 | 3/1987 | Senoue et al. | 5/453 |
| 4,694,520 | 9/1987 | Paul et al. | 5/453 |
| 4,711,275 | 12/1987 | Ford et al. | 5/453 X |
| 4,833,457 | 5/1989 | Graebe, Jr. | 5/455 X |
| 4,852,195 | 8/1989 | Schulman | 5/453 |
| 4,982,466 | 1/1991 | Higgins et al. | 5/453 |
| 5,044,029 | 9/1991 | Vrzalik | 5/453 |

*Primary Examiner*—Michael F. Trettel
*Attorney, Agent, or Firm*—Bernard L. Kleinke; Jerry R. Potts

[57] ABSTRACT

A mattress, which is particularly effective in preventing and relieving decubitus ulcers, comprises a plurality of inflatable sections. Inflation means associated with the mattress inflate at least one of the inflatable sections at a first, higher pressure and simultaneously inflate at least one of the inflatable sections at a second, lower pressure. By sequentially changing the sections to which the high and low pressures are applied, different areas of a patient's body may be pressure relieved in turn, allowing blood to flow in the parts of the patient in contact with a low pressure section, while still providing support for the patient. There may be a number of groups of sections, all the sections in each group being interconnected, and each group being sequentially inflated at the lower pressure for a preset period.

16 Claims, 4 Drawing Sheets

INFLATABLE MATTRESS AND AIR SUPPLY WITH CHANGEOVER VALVE

DESCRIPTION

The present invention relates to mattresses, and in particular, but not exclusively, to mattresses for the prevention of, and relief from, decubitus ulcers.

Decubitis ulcers occur when blood flow through the skin capillaries is occluded by virtue of the fact that tissue is compressed for a prolonged period by the weight of the person and a support surface. A person who is healthy responds to nervous signals from the area of tissue in question when the tissue has been compressed for some time, and the person will thus automatically shift position to relieve the compressed area, thereby enabling blood flow to recommence. This procedure repeats itself indefinitely.

However, people without the ability to move themselves, e.g. comatose, obtunded or severely disabled people, cannot relieve the pressure in this way, and thus if they are allowed to remain in the same position, parts of the tissue die and become ulcerated, producing what are commonly termed 'pressure sores'. The problem also arises with elderly people who have restricted movement. The problem is exacerbated by diet, immobility, possible low blood pressure/volume and poor skin perfusion.

The traditional way of preventing or relieving bed pressure sores has been to turn the patient frequently, thus causing a different area of the patient to be compressed from time to time. However, this is not always practical or possible.

An alternative way is to place the patient on an overlay, with a view to contacting more areas of the body in order to spread the patient's weight. However, although such an overlay is comfortable, it frequently does not prevent or relieve pressure sores, since the pressure relief obtained in the areas most at risk (e.g. bony prominences) is very often insufficient to enable re-establishment of the blood flow.

A number of prior art devices have attempted to overcome the aforementioned problems. However, the prior art devices involve alternate inflation and deflation of a number of inflatable cells. Allowing cells to deflate causes problems in that a deflated cell provides no support at all, with the result that it is possible for a person, particularly a heavy person to engage a supporting surface below the device in the region of a deflated cell, thus providing no pressure relief. On the other hand, it has been known for very light persons to slip through the gap between two inflated cells in the region of a deflated cell, which can be most uncomfortable and unnerving.

It is an object of the present invention to provide a mattress which assists in the prevention and relief of pressure sores, but which overcomes the problems of known mattresses.

In accordance with a first aspect of the present invention, a mattress comprises a plurality of inflatable sections and inflation means for inflating one or more of the inflatable sections at a first, higher pressure and for simultaneously inflating one or more of the inflatable sections at a second, lower pressure.

Preferably, the inflation means is adapted to supply the higher pressure and lower pressure at different times to each of the inflatable sections. In one embodiment, the sections comprise a plurality of groups (e.g. three) of interconnected sections, and the inflation means is adapted to supply all but one of the groups with the higher pressure and simultaneously to supply one of the groups with the lower pressure. The inflation means also changes sequentially the group to which the lower pressure is applied, so that the lower pressure is applied in turn to each of the groups.

In this way, the area of a patient in the region of a section which is inflated at the lower pressure is pressure relieved to a greater extent than the sections at the higher pressure, whilst still providing a support area.

There may also be means for altering the time for which the lower pressure is applied to each section or group of sections. Furthermore, there may be pressure sensitive means adapted to detect a drop in pressure and audible and/or visual warning means actuated in response to a signal from the pressure sensitive means. This arrangement indicates when a patient has, for example, fallen from or left the mattress.

In accordance with a second aspect of the present invention, a method of inflating an inflatable mattress comprising a plurality of inflatable sections comprises inflating one or more of the sections at a first, higher pressure and simultaneously inflating one or more of the sections at a second, lower pressure, and sequentially changing the section or sections to which the higher and lower pressures are applied.

The method may involve inflating all but one of a number of groups of sections at the higher pressure and inflating the remaining group of sections at the lower pressure, and sequentially changing the group to which the lower pressure is applied.

By way of example only, a specific embodiment of the present invention will now be described, with reference to the accompanying drawings, in which.

The mattress comprises a plurality of elongate inflatable hollow tubular sections 10, each formed from flexible polyurethane sheeting which is radio-frequency welded into the desired shape and configuration. The ends of the base wall of each of the sections 10 extend beyond the respective end walls, thereby forming a tag 11. Each tag 11 is provided with one component 12 of a snap-fastener, the other components being secured in predetermined locations on the base wall of a mattress cover 14 which will be described in more detail later. The sections are thus held in position such that they lie parallel to one another to form the mattress as illustrated, with the sections 10 extending transversely to the longitudinal direction of the bed.

Figure 1:
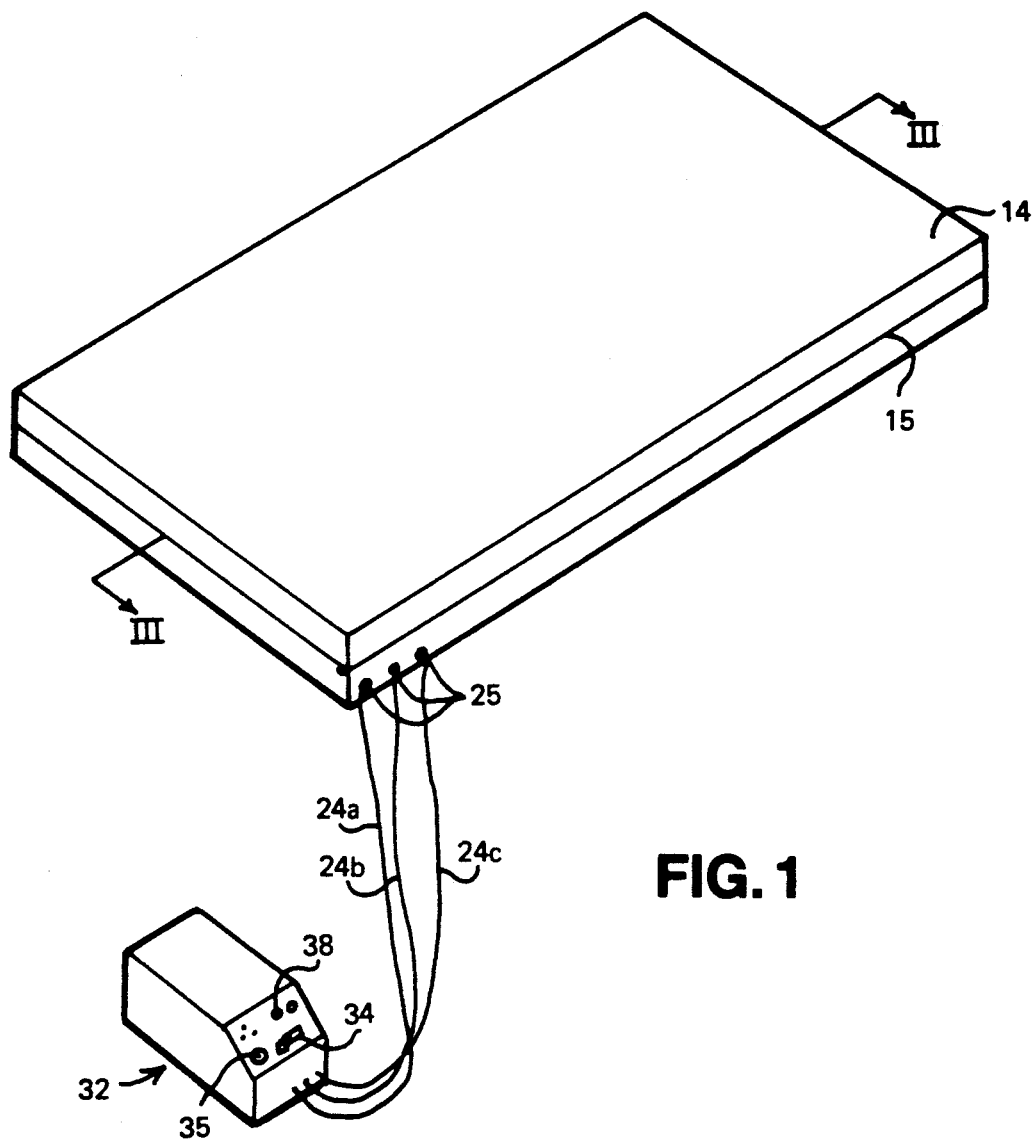
FIG. 1 is a perspective view of an embodiment of mattress in accordance with the present invention.
Figure 3:
FIG. 3 is a cross-sectional view in the direction of arrows III—III of FIG. 1.
Figure 2:
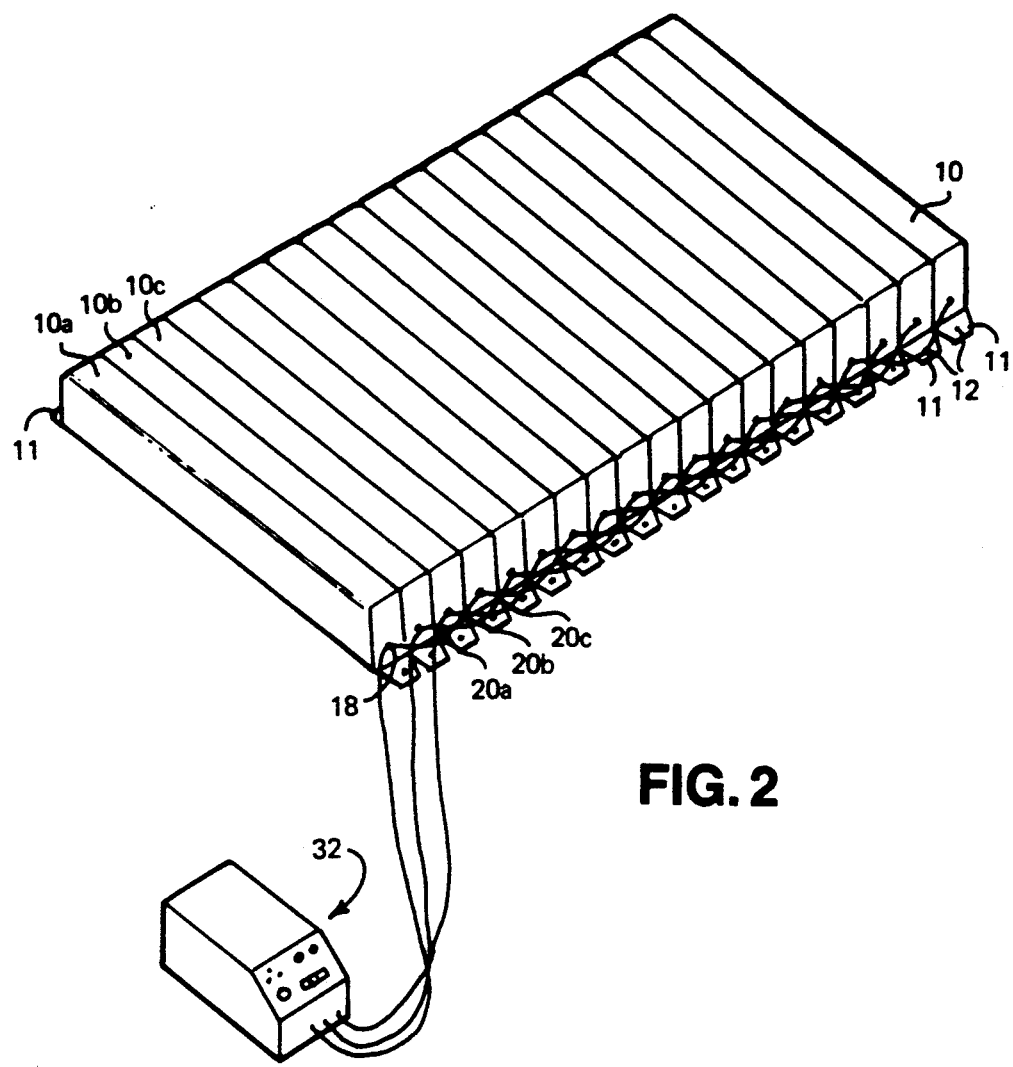
FIG. 2 is an exploded perspective view of the mattress of FIG. 1, with its cover removed.

As shown in the Figures, the sections 10 are generally rectangular in cross-section, and thus adjoining faces of adjacent sections are pressed tightly in contact with one another when the sections of the mattress are inflated. In use, the mattress is housed within the removable flexible cover 14 whose upper and side walls are made from microporous vapour permeable material. The cover 14 is constructed of upper and lower parts, which are releasably joined by elongate zip fasteners 15 extending along opposite side edges of the cover, (one of which is visible) and hook and loop fasteners (not visible) in the vicinity of the joint between the upper and lower parts along the end edges. As explained above, the mattress may be releasably held in the correct position within the cover by means of complementary snap fastener components located on the tags extending from the end walls of the sections and on the base wall of the mattress cover 14. In this way, the mattress is prevented from slipping with respect to the cover, but may still be easily removed when desired. As shown in FIG. 3, a foam layer 16 may also be inserted between the sections 10 and the lower wall of the cover.

One end of each of the tubular sections 10 is provided with a T-connector 18 which communicates with the interior of the section. Groups are formed from sequentially arranged sections 10a, 10b, 10c such that every third section is part of the same group and is connected to adjacent sections of that group by means of flexible tubing 20a, 20b, 20c respectively extending between the relevant T-connectors 18. The three sections 10 adjacent to one end of the mattress are supplied with pressurised air from a pump unit 32 by means of respective flexible tubing 24a, 24b, 24c which pass through apertures 25 in the side of the cover 14. As will be explained, the pump unit is adapted to control the pressure in the three groups of inflatable sections 10, such that the pressure is either a first, higher pressure or a second, lower pressure.

Figure 4:
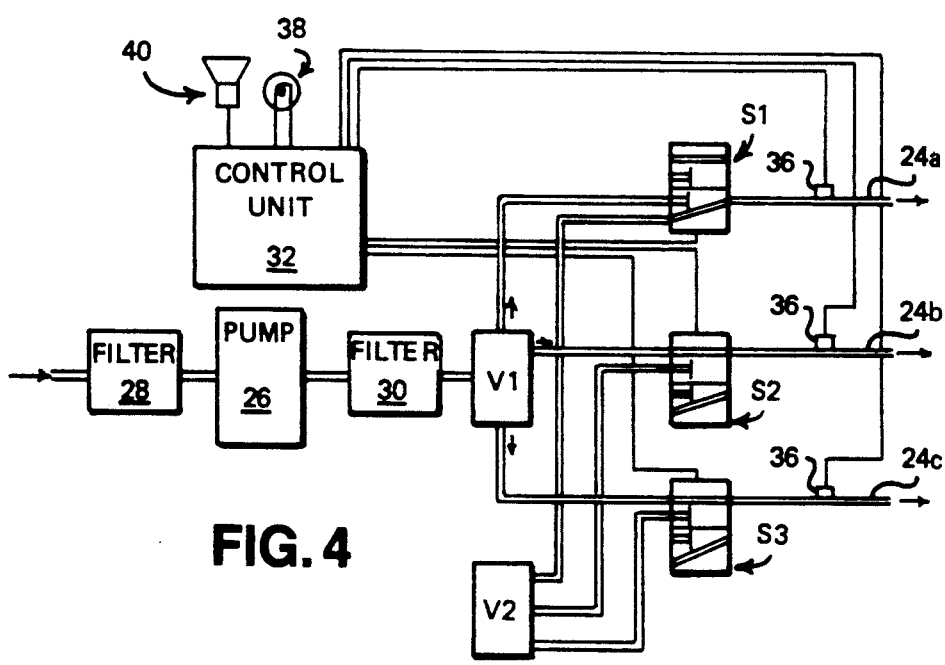
FIG. 4 is a diagrammatic illustration of means for inflating the mattress of FIG. 1.

The pump unit is illustrated schematically in FIG. 4, and comprises an electrically driven pump 26 which draws in air via a first filter 28 and expels pressurised air via a second filter 30. The pressurized air is fed to a first conventional pressure relief valve $V_1$ which limits the pressure output from it to a first, higher pressure $P_1$ of, for example, 20 to 30 mm of mercury, typically 28 mm. This fixed pressure is fed to one inlet port of each of three 3/2 (three port, two position) solenoid-actuated valves, $S_1$, $S_2$, $S_3$. The inputs of a second conventional pressure relief valve $V_2$, which limits the pressure output from it to a second lower pressure $P_2$ of, for example, 10 to 15 mm of mercury, typically 14 mm, are connected respectively to the other inlet port of each of the three solenoid valves $S_1$, $S_2$, $S_3$.

Figure 5:
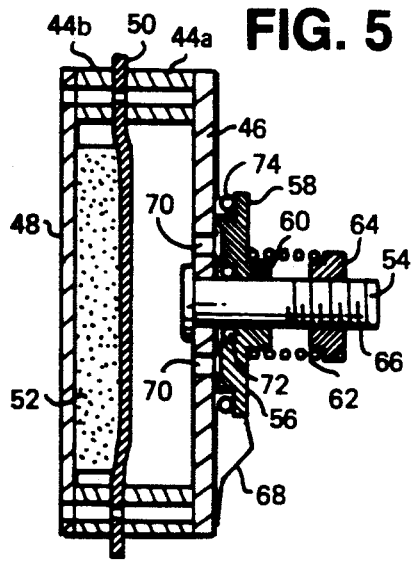
FIGS. 5 and 6 are a cross-sectional side elevation and a plan view respectively of a first pressure relief valve of the embodiment of FIG. 1.
Figure 6:
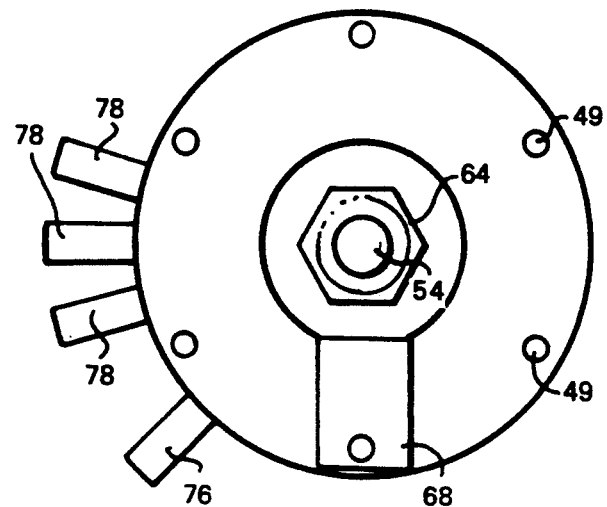

The pressure relief valve $V_1$ is shown in FIGS. 5 and 6. The valve comprises a cylindrical valve body having a cylindrical side wall 44 and disc-shaped upper and lower end walls 46, 48. The side wall 44 is in two portions 44a, 44b between which is sandwiched a circular diaphragm 50 made from fabric-reinforced rubber sheeting. A foam rubber pad 52 is located between the diaphragm 50 and the lower end wall 48. The valve body components are held together by means of six equally spaced screws 49 passing through aligned apertures in the upper end wall 46, the upper side wall portion 44a, the diaphragm 50, the lower side wall portion 44b and the lower end wall 48.

The upper end wall is provided with a metal spigot 54 which is cemented to the upper end wall 46 and passes through the wall perpendicularly to the plane of the wall. The portion of the spigot nearest to the end wall 46 is cylindrical and a valve closure member 56 is slidably disposed thereon. The valve closure member 56 comprises a disc-shaped portion 58 and a collar 60. The valve closure member 56 is biassed towards the end wall 46 by means of a compression spring 62 extending between the upper face of the valve closure member 56 and the lower face of an adjustment member 64 which is threadedly mounted on a threaded end portion 66 of the spigot 54. By suitable rotation of the adjustment member the biassing force can be altered. A further, non-adjustable biassing force is provided by means of a leaf spring 68 which bears on the upper surface of the valve closure member and is held in position by one of the screws 49.

The upper end wall 46 is provided with six equally angularly-spaced spill ports 70 arranged in a circular pattern around the spigot 54. When the valve closure member 56 is held in contact with the upper face of the upper end wall 46, the spill ports 70 are closed by means of O-rings 72, 74 located on the valve closure member 56 radially inwardly and outwardly respectively of the spill ports 70. When the pressure in the spill ports is sufficient to displace the valve closure member 56 against the biassing force of the two springs 62, 68, the ports are exhausted to atmosphere.

The valve body is also provided with an inlet port 76 from the pump 26 and three outlet ports 78, each outlet port leading to a respective one of the solenoid valves $S_1$, $S_2$, $S_3$. It will be appreciated that the valve $V_1$ thus enables an upper limit to be placed on the pressure supplied to the solenoid valves $S_1$, $S_2$, $S_3$.

Figure 7:
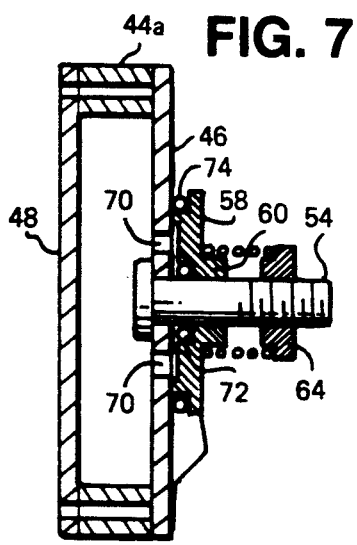
FIGS. 7 and 8 are a cross-sectional side elevation and a plan view respectively of a second pressure relief valve of the embodiment of FIG. 1.
Figure 8:
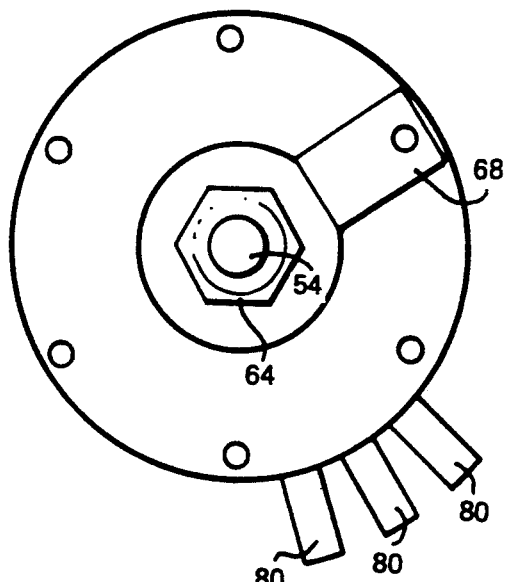

The pressure relief valve $V_2$, illustrated in FIGS. 7 and 8, is very similar to the valve $V_1$, and the same reference numerals have been used to identify similar or identical features. The main difference is that the lower side wall portion 44b, the diaphragm 50 and the foam pad 52 have been omitted for the valve $V_2$. Also, the valve $V_2$ has three inlet ports 80, one from each of the solenoid valves $S_1$, $S_2$, $S_3$. It will thus be appreciated that when the solenoid valves $S_1$, $S_2$, $S_3$ are in the positions of the valves $S_1$ in FIG. 4, the maximum value of the pressure in the respective inflatable tubular sections can be limited.

Figure 9:
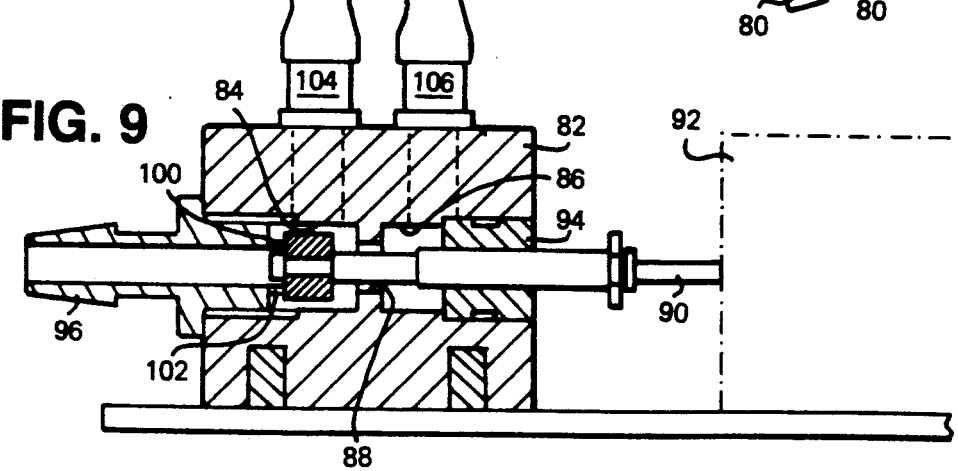
FIG. 9 is a cross-sectional side elevation of a solenoid-actuated valve of the embodiment of FIG. 1.

One of the three identical solenoid valves $S_1$, $S_2$, $S_3$ is illustrated in FIG. 9. The valve comprises an elongate valve body 82 which is hexagonal in cross-section. The valve body 82 is provided with two longitudinally extending bores 84, 86 in its opposite end faces. Each of the bores 84, 86 is stepped such that they are wider in the region adjacent to their respective end faces and the two bores communicate by means of a connecting bore 88.

The output rod 90 of a solenoid actuator 92 is slidably and sealingly displaceable in a PTFE bushing 94 which is secured in the bore 86 by means of adhesive. An output nozzle 96 is secured in the bore 98 by means of adhesive. A tubular rubber seal 100 is located on the end of the solenoid rod 90. In one extreme position of the rod, illustrated in FIG. 9, the seal 100 abuts a tubular extension 102 of the nozzle and in a second extreme position the seal 100 blocks off the connecting bore 88.

It will also be noted that two other nozzles 104, 106 are provided on the valve body, each nozzle communicating with a respective one of the two bores 84, 86.

The nozzle 104 is connected in use to one of the sections 10a, 10b, 10c; the nozzle 106 is connected to the output of the valve $V_1$; and the nozzle 96 is connected to the valve $V_2$.

In the first extreme position, illustrated in FIG. 9, the output of the valve $V_1$ is thus supplied to one of the sections 10a, 10b, 10c via the nozzle 104, the connection to the valve $V_2$ being isolated by means of the tubular valve seal 100. In the second extreme position, the seal 100 abuts the periphery of the connecting bore 88 thus isolating the pressure in nozzle 106 from the nozzle 104 and connecting the nozzle 104 with the valve $V_2$, and thus limiting the pressure in the section 10a, 10b and 10c to the pressure set by valve $V_2$.

The outlet ports of the three solenoid valves $S_1$, $S_2$, $S_3$ are connected to the flexible tubing 24a,24b,24c respectively of the three groups of hollow tubular sections 10a, 10b,10c. As illustrated in the figures, in one position of the valves, the higher pressure from valve $V_1$ is fed to the outlet port, but in the other position, the position illustrated by solenoid $S_1$, the outlet port is connected instead to valve $V_2$, thereby limiting the pressure in the outlet to that set by $V_2$. The position of the solenoid actuated valves $S_1$, $S_2$, $S_3$, is controlled by means of an electronic control unit 32 which is arranged to actuate the solenoid of valves $S_1$, $S_2$, $S_3$, sequentially to their alternative positions, wherein the lower pressure is applied to the output, for a desired period of time as determined by the control unit 32.

Figure 10:
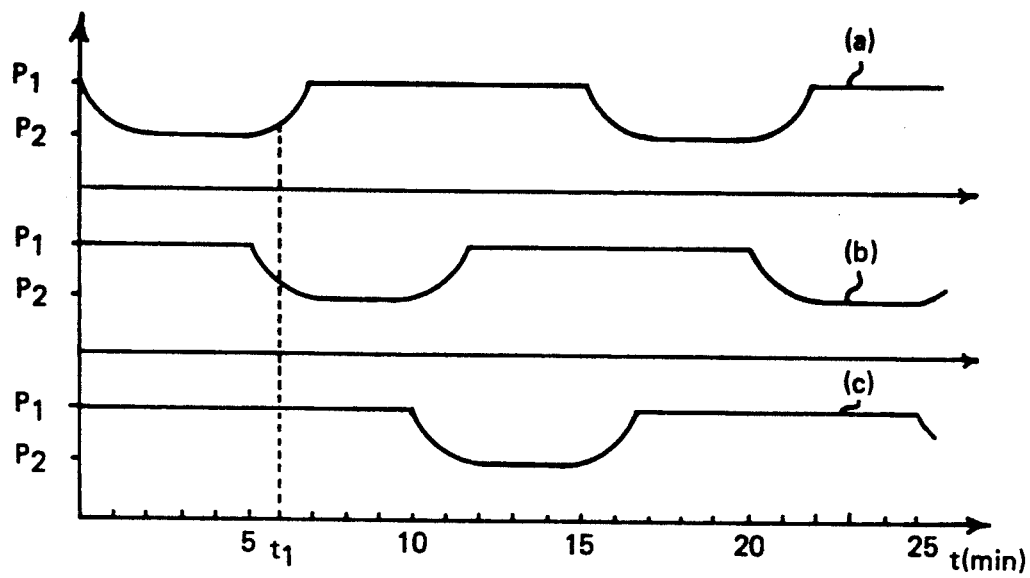
FIGS. 10 and 11 are graphs of pressure against time in two alternative operational modes of the embodiment of FIG. 1.

In this embodiment the control unit is able to control the inflation of the sections 10 in two alternative modes, depending upon the circumstances. The first mode is illustrated in FIG. 10, which illustrates the variation with time of the pressures applied to the three groups of sections 10. It will be noted that the changeover from higher pressure ($P_1$) to lower pressure ($P_2$) is not instantaneous, in view of the large volume of air within each of the groups of sections 10. In the first mode, it will be noted that the high to low changeover in pressure in one group commences before the low to high changeover in pressure in the group which was previously inflated at the lower pressure is complete. In this way, it will be noted that for part of the cycle (e.g. at time $t_1 \approx 6$ minutes) one group only is inflated at the full higher pressure whilst the pressure in another group is falling from the higher pressure to the lower pressure and the pressure in the third group is rising from the lower pressure to the higher pressure.

Figure 11:
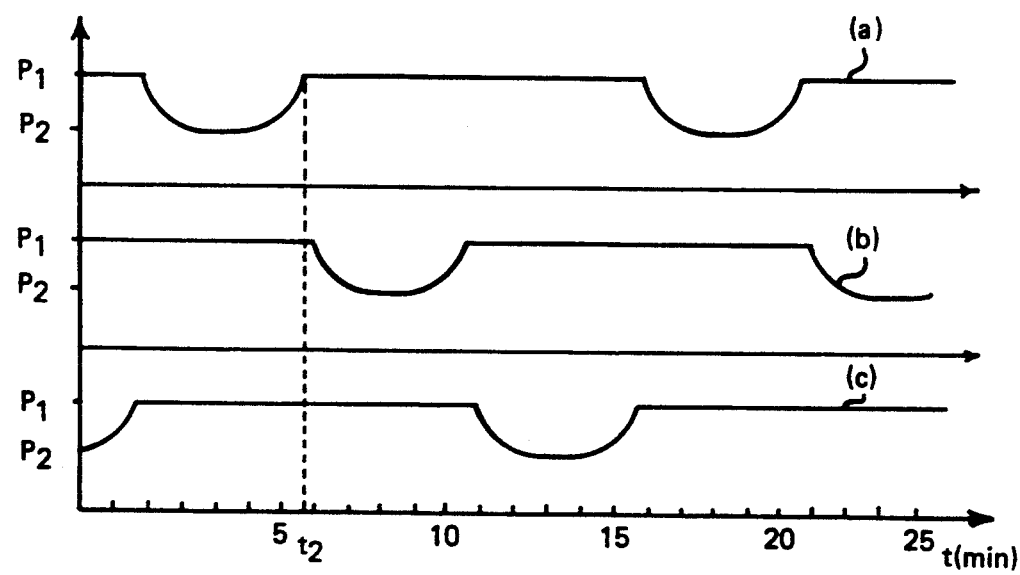

In the alternative mode, illustrated in FIG. 11, the high to low changeover in pressure in one group does not commence until the low to high changeover in pressure in the group previously inflated at the lower pressure is complete. In this way, only one group of sections is ever inflated at the lower pressure at any one time, and for a very short period of time (e.g. at $t_2 \approx 6.7$ minutes), the three groups are all inflated at the higher pressure.

The two alternative modes do not rely on pressure sensors, but merely on appropriate timing in the control unit in order to operate the solenoid valves $S_1$, $S_2$, $S_3$ at the appropriate times. For the first mode of operation, each solenoid valve $S_1$, $S_2$, $S_3$ is actuated in turn to its alternative position (in which the output is connected to the valve $V_2$) for five minutes. In the alternative second mode, when one solenoid valve moves back to its higher pressure position, to connect valve $V_1$ to the output, the control unit delays operation of the next solenoid valve into its lower pressure position by two minutes, thus ensuring that all the groups are temporarily inflated at the higher pressure before the next solenoid valve is actuated in order to inflate one of the groups at the lower pressure.

The selection of modes is carried out by means of a rocker switch 34 which selects one or other of the modes. There may also be a control 35 for adjusting the time for which each solenoid valve is in its lower-pressure position, although this feature may be omitted if desired. The first mode is used for most patients when they are lying down. The second mode is used for heavy patients and for when patients are sitting up, since it is sometimes possible for a patient to "bottom out" and engage the bed itself through the mattress in such circumstances if two adjacent sections are only partially inflated.

In this way, the groups of sections 10a,10b,10c are inflated at the lower pressure, rather than at the higher pressure when the respective valve $S_1$, $S_2$, $S_3$ is in its alternative position. The region of a person on top of the section which is inflated at the lower pressure is thus not pressurised as much, and enables blood to move easily in that area whilst still giving support. The majority of the weight is supported by the sections inflated at the higher pressure. As this happens in turn with each of the three groups, every area of the patient is pressure-relieved in turn, and thus blood flows more easily in such areas on a regular basis, thus preventing the formation of bed sores and allowing existing sores to heal.

It will also be noted that each of the flexible output tubes 24a,24b,24c is provided with a pressure sensor 36 which is adapted to close a switch when the pressure in the corresponding tube falls below a preset pressure, typically a few mm below the lower of the two pressures. In this way, if a patient should move from the mattress, resulting in a significant drop in pressure in the sections 10, one or more of the pressure sensors is activated, thus sending a signal to the control unit 32, which is adapted to actuate a lamp 38 and/or a loudspeaker 40 with a warning tone. Thus, if a patient falls from the bed, or leaves the bed having been advised not to, for example, this is immediately apparent. The sensors, do, however, allow a variation in the pressure before being actuated, so that normal movement of a patient on a mattress will not activate the visual or audible alarms.

The present invention also has the significant advantage that if air is displaced from one of the sections (e.g. by a person sitting up and thereby concentrating most of the body weight in a small area) the air in the sections of that group is not allowed to reach a pressure higher than that specified by the valve $V_1$ or $V_2$ to which it is connected as that time. Since $V_1$ and $V_2$ are pressure relieving valves, they act so as to reduce the air pressure to the maximum predetermined pressure, whilst still providing support. If this were not the case, then displacement of air from one of the sections could result in an increase in pressure within all of the sections of that group, which in turn could result in occlusion of blood flow to the capillaries, with the danger of pressure sores.

I claim:
1. A mattress comprising:
   a plurality of inflatable sections; and
   inflatable means which in use inflates at least one of the inflatable sections at a first, higher pressure and simultaneously inflates at least one of the inflatable sections at a second, lower pressure;
   wherein said inflatable means includes:

a pump;

a first pressure limiting valve connected to said pump for limiting pressure to inflatable sections at said first, higher pressure;

a second pressure limiting valve for limiting pressure to the inflatable sections at said second, lower pressure; and a plurality of changeover valves, each changeover valve being connected to at least one of said inflatable sections and being operable to connect either said first pressure limiting being operable to connect either said first pressure limiting valve or said second pressure limiting valve to each inflatable section connected to the changeover valve.

2. A mattress according to claim 1, wherein said inflatable means supplies said first higher pressure and said second, lower pressure at different times to each of said plurality of inflatable sections.

3. A mattress according to claim 2, wherein said inflation means sequentially changes the sections to which said higher pressure and lower pressure are supplied.

4. A mattress according to claim 3, wherein a changeover from higher pressure inflation to lower pressure inflation for a section overlaps with a changeover from lower pressure inflation to higher pressure inflation for a different section.

5. A mattress according to claim 3, wherein a changeover from higher pressure inflation to lower pressure inflation for a section does not overlap with a changeover from lower pressure to higher pressure for a different section.

6. A mattress according to claim 1, further comprising:
means for altering selectively the time each one of said plurality of inflatable sections is inflated at said second, lower pressure.

7. A mattress according to claim 1, further comprising:
a plurality of groups of interconnected inflatable sections, the pressure within each group of sections being substantially equal.

8. A mattress according to claim 7, wherein said plurality of groups of interconnected inflatable sections includes at least three groups of inflatable sections.

9. A mattress according to claim 7, wherein said inflatable means inflates at least one group of sections at said second, lower pressure, and inflates at least another group of sections at said first, higher pressure.

10. A mattress according to claim 1, further comprising:
a pressure detector for detecting a drop in pressure in the mattress to a predetermined level; and
indicating means for providing a user sensed warning of low pressure.

11. A mattress according to claim 1, wherein said plurality of changeover valves are solenoid-actuated valves.

12. A mattress according to claim 1, further comprising:
a control means for controlling the operation of said inflatable means.

13. A method of inflating an inflatable mattress having a plurality of inflatable sections, comprising:
inflating at least one of the inflatable sections at a first higher pressure;
inflating simultaneously at least another one of the inflatable sections at a second lower pressure; and
connecting a first pressure limiting valve to a pump for limiting the pressure applied to the inflatable sections at said first, higher pressure;
connecting a second pressure limiting valve to said pump;
connecting a plurality of changeover valves between the plurality of inflatable sections and said first pressure limiting valve and said second pressure limiting valve;
changing the pressure applied to each inflated section sequentially between said first higher pressure and said second lower pressure.

14. A method according to claim 13, wherein a changeover from higher pressure inflation to lower pressure inflation for a section overlaps with a changeover from lower pressure inflation to higher pressure inflation for a different section.

15. A method according to claim 13, wherein a changeover from higher pressure inflation to lower pressure inflation for a section does not overlap with a changeover from lower pressure inflation to higher pressure inflation for a different section.

16. A method according to claim 13, further comprising:
interconnecting the inflatable sections to form a plurality of groups of sections, wherein the pressure within the sections of each group is substantially equal.

* * * * *